United States Patent [19]

Powell et al.

[11] Patent Number: 5,185,028
[45] Date of Patent: Feb. 9, 1993

[54] N-ACYL LOLINE DERIVATIVES AS INSECTICIDES AND HERBICIDES

[75] Inventors: Richard G. Powell; Richard J. Petroski, both of Peoria, Ill.

[73] Assignee: The United States of America, as represented by the Secretary of Agriculture, Washington, D.C.

[21] Appl. No.: 747,220

[22] Filed: Aug. 19, 1991

[51] Int. Cl.$^5$ .................. C07D 491/18; A01N 43/90
[52] U.S. Cl. ................................. 504/284; 514/411; 548/428
[58] Field of Search ............... 548/428; 514/411; 71/95

[56] References Cited

PUBLICATIONS

Takeda et al., Chem. Pharm. Bull., 39(4)7 pp. 964-968 (Apr. 1991).
R. C. Larock, "Comprehensive Organic Transformations: A Guide to Functional Group Preparations", VCH Publishers, NY, 1989, pp. 901-902.
T. Matsuzaki et al., "Germination and Growth Inhibition of Acylnornicotines from Section Repandae of the Genus Nicotiana and Synthetic Acylnornicotines", Agric. Biol. Chem. 52(8), 1899-1903, 1988.
Richard J. Petroski et al., "Germination and Growth Inhibition of Annual Ryegrass (*Lolium multiflorum* L.) and Alfalfa (*Medicago sativa* L.) by . . ." J. Agric. Food Chem. 38:1716-1718 (1990).
W. E. Riedell et al., "Naturally-Occurring and Synthetic Loline Alkaloid Derivatives: Insect Feeding Behavior Modification and Toxicity," J. Entomol, Sci. 26(1):122-129 (1991).
R. J. Petroski et al., "Isolation, Semi-Synthesis, and NMR Spectral Studies of Loline Alkaloids," J. Nat. Prod. 52(4):810-817 (Jul.-Aug. 1989).
Shelly G. Yates et al., "Assay of Tall Fescue Seed Extracts, Fractions, and Alkaloids Using the Large Milkweed Bug," J. Agric. Food Chem. 37:354-357 (1989).

*Primary Examiner*—Joseph Paul Brust
*Assistant Examiner*—MarySusan H. Gabilan
*Attorney, Agent, or Firm*—M. Howard Silverstein; Randall E. Deck; John D. Fado

[57] ABSTRACT

N-substituted loline derivatives having the formula

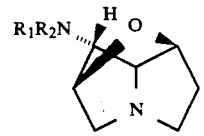

have utility as herbicides and insecticides.

32 Claims, No Drawings

N-ACYL LOLINE DERIVATIVES AS INSECTICIDES AND HERBICIDES

BACKGROUND OF THE INVENTION

Numerous secondary plant constituents inhibit the growth and development of other organisms. Constitutive and induced compounds protect the donor plant from stress imposed by insects, fungi, herbivores, and competing plants, [Bailey et al., Phytoalexins, 1982, New York; Rice, Allelopathy, 1984, Academic, Florida; Powell et al., ACS Symp. Ser. 380, 1988, pages 211-232]. Saturated pyrrolizidine alkaloids of the loline type occur in relatively high concentrations in tall fescue that is infected with Acremonium coenophialum [Petroski et al., J. Nat. Prod. 52: 810-817 (1989)], but they have not been detected in tall fescue in the absence of this fungus. The lolines have not been considered contributors to the observed allelopathy of tall fescue [Peters, Crop Sci. 8: 650-653 (1968); Peters et al., Agron. J. 73(1): 56-58 (1981); Walters et al., J. Chem. Ecol. 2: 469-479 (1976)].

The plant kingdom uses chemical substances as defenses against insects [Jacobson, Econ. Bot. 36: 346-354 (1981)]. A recent report which outlined one such plant-insect relationship [Johnson et al., Appl. Environ. Microbiol. 49: 568-571 (1985)] indicated that tall fescue plants infected with an endophytic fungus produced compounds which deter feeding aphids and milkweed bugs. In an effort to identify the compounds which were active in deterring feeding, these authors prepared extracts of tissue from endophyte-infected plants. Because the extracts contained a mixture of alkaloid types, active compounds were not specifically identified.

Using extracts from seeds of endophyte-infected plants, Yates et al. [J. Agric. Food Chem. 37: 354-357 (1989)] showed that N-formylloline and related alkaloids were potent toxins to milkweed bugs. Further fractionation of the extracts revealed the presence of several derivatives of loline, namely N-methylloline and N-acetylloline, as well as N-formylloline [Yates et al., J. Agric. Food Chem. 38: 182-195 (1990)].

SUMMARY OF THE INVENTION

We have found a plurality of synthetic N-acylloline derivatives that are significantly phytotoxic against seedling growth of alfalfa and annual ryegrass. Quite unexpectedly it has been found that the synthetic N-acylloline derivatives of this invention are phytotoxic as generally compared to the group of naturally occurring loline derivatives which have been previously described (namely loline, formylloline, acetylloline, methylloline, and other norloline derivatives). Norloline and N-formylloline exhibit no phytotoxicity against seedling growth of alfalfa and annual ryegrass at doses up to $1 \times 10^{-6}$ mol/seed. N-acetylloline and N-methylloline exhibit no phytotoxicity at doses between $0.1 \times 10^{-8}$ mol/seed and $100 \times 10^{-8}$ mol/seed. However, N-formylloline inhibited germination of annual ryegrass when used at relatively high doses; the $ID_{50}$ value was $77 \times 10^{-8}$ mol/seed. Surprisingly, N-acyl derivatives of loline having between nine and fourteen carbon atoms in a straight chain exhibited substantially greater phytotoxicity. Included in the testing were N-cinnamoyl and N-(p-n-hexylbenzoyl) derivatives of loline.

In accordance with this discovery, it is an object of this invention to provide a number of loline derivatives having significant herbicidal and insecticidal activity.

DETAILED DESCRIPTION OF THE INVENTION

In the practice of the present invention, the loline derivatives are characterized by the following formula,

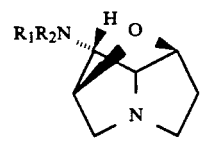

wherein $R_1$ is a $C_4$ to $C_{20}$ aliphatic, aromatic, or alicyclic hydrocarbon optionally substituted with oxygen, and $R_2$ is hydrogen, or an aliphatic, aromatic, or alicyclic hydrocarbon also optionally substituted with oxygen. The $R_1$ and $R_2$ groups may be saturated or unsaturated, and straight or branched chains. Compounds wherein $R_1$ is a straight chain $C_9$ to $C_{14}$ acyl group and $R_2$ is hydrogen or particularly methyl are especially preferred.

As a practical matter it is envisioned that compositions of the instant compounds would be prepared by adding the compound to a suitable solvent, as an inert carrier. Agronomically acceptable solvents include alcohols, ketones, esters, and aqueous surfactant mixtures. The concentration of the compound in the final composition may vary considerably, but should be at least 10 ppm and preferably greater than 100 ppm.

Depending on the effect desired, the instant compounds can be directly applied to plants, seeds, or insects, or the compound can be applied to the locus of the plant, seed, or insect. The compound is administered in an amount effective to induce the desired response and is predetermined by routine testing. Where the ultimate response is plant, seed, or insect mortality, an "effective amount" or "insecticidally (herbicidally) effective amount" is defined to mean those quantities which will result in a significant mortality to a test group compared to an untreated group. The actual effective amount may vary with the species, stage of development, environmental conditions, nature of substrate, type of carrier, period of treatment, and other related factors.

To be effective the compound must be applied to the locus of, or the vicinity of, the plant or insect to be controlled. When the compound is intended as an insecticidal stomach poison, it is applied in conjunction with its carrier to the insect diet. In the case of insects on plants, the composition will typically be applied to leaf surfaces or else systemically incorporated. Alternatively, when the compound is to be used as a contact poison, any method of topical application, such as direct spraying on the insect or a substrate which is likely to be contacted by the insect, would be appropriate.

The compounds encompassed herein are effective in controlling a variety of insects and plants. Without being limited thereto, it is envisioned that the compounds will be particularly effective against insects of the families Pyralidae and Noctuidae, and plants of the families Gramineae and Fabaceae.

The N-acylloline derivatives were prepared as described by Petroski et al. [J. Agric. Food Chem., 38(8):

1716–1718 (1990)], the contents of which are incorporated by reference herein. In review, the appropriate acid chloride (10 mmol) was added to a solution of loline (1.54 g, 10 mmol) in 10 mL of $CHCl_3$ and stirred at 25° C. for 48 hr. The reaction mixture and a 20 mL aqueous wash of the reaction flask were then poured into a 100 mL beaker, and the pH of the aqueous phase was adjusted to 10 with NaOH. The $CHCl_3$ phase was collected, and the alkaline aqueous solution was extracted three more times with 20 mL of $CHCl_3$. The $CHCl_3$ extracts were combined and dried over anhydrous $Na_2SO_4$ and then $CHCl_3$ was removed by evaporation, in vacuo, to afford the desired product.

The purity of each loline derivative was determined by capillary GC using conditions previously described for the analysis of loline derivatives that occur naturally by Petroski et al. [J. Nat. Prod. 52: 810–817 (1989)], the contents of which are incorporated by reference herein. N-Benzoylloline was recrystallized from carbon tetrachloride-cyclohexane. N-Octanoylloline, N-decanoylloline, N-dodecanoylloline, N-tetradecanoylloline, N-hexadecanoylloline, and N-(p-n-hexylbenzoyl)loline were each chromatographed on silica gel (10 g) gravity columns using chloroform to elute impurities, followed by $CHCl_3$-MeOH (80:20) to elute the purified product. The structure of each compound was confirmed by IR, NMR, and GC/MS. All loline derivatives were greater than 99% single components as determined by capillary GC.

A 5 mM stock solution of loline and several loline derivatives were prepared by dissolving the appropriate weight in $CHCl_3$ and diluting with hexane to 1:99(v/v) $CHCl_3$-hexane. A dilution series was made from the stock solution of each test compound with the same solvent composition to give a dosage series in concentrations from 0.05 to 5 mM.

Alfalfa seeds were imbibed for 4 hr on two layers of 9-cm diameter Whatman No. 1 filter paper that was saturated with water. The preimbibition treatment was necessary to select seeds permeable to water, so that failure to germinate could more accurately be attributed to a test compound effect. Annual ryegrass seeds were not preimbibed because the seeds exhibited no hardseededness.

The bioassay used to determine phytotoxicity of each exogenously applied loline derivative was similar to that described previously by Dornbos et al. [J. Chem. Ecol. 16(2): 339–352 (1990)], the contents of which are incorporated by reference herein. Bactoagar (4.4 g; Difco Laboratory, Detroit, MI) was dissolved in water (400 mL) by autoclaving at 121° C. for 20 min and then diluting with an additional 400 mL of water. One milliliter of the resulting agar solution was pipetted into each 4 mL glass vial and allowed to harden. Test compounds, contained in 1 mL solvent and solvent controls, were carefully layered on top of the hardened agar, and the solvent was allowed to passively evaporate in a ventilated hood.

Five alfalfa or annual ryegrass seeds were placed on the agar in each vial. Alfalfa, a dicot, and annual ryegrass, a monocot, were selected as test species to indicate any broad spectrum inhibition by the compounds tested. The vials were capped (small holes were punctured in the vial caps) and placed in a growth chamber in darkness at a constant temperature of 30° C. After 3 days, seeds with a radicle protruding through the seed coat were counted as germinated. The length of each seedling (root plus shoot) was measured to the nearest millimeter.

All experiments were conducted as completely randomized designs with four or six replications. Treatment effects were considered significant when $P \leq 0.05$ as determined by the General Linear Model (Standard Anova) procedure of the Statistical Analysis System (SAS Institute, Inc.). A regression equation describing the linear reduction of germination percentage and seedling length of each compound was calculated if the germination percentage or seedling length was reduced significantly by increased doses. Doses that caused 50% inhibition ($ID_{50}$) in germination and in seedling growth were calculated from each regression equation.

Phytotoxicity of loline derivatives was tested against a broadleaved plant and against a grass to detect any general selectivity. To facilitate comparison of seeds from different plant species that vary in mass, dose was calculated in moles per gram of seed dry weight. The $ID_{50}$ of (p-n-hexylbenzoyl)loline against germination of annual ryegrass was $2.4 \times 10^{-5}$ mol/g, and that of alfalfa was $43.3 \times 10^{-5}$ mol/g. This compound is nonselectively phytotoxic to alfalfa and annual ryegrass seedling length exhibiting $ID_{50}$ values of $2.0 \times 10^{-5}$ and $4.2 \times 10^{-5}$ mol/g of seed, respectively. The seedling growth $ID_{50}$ values for N-octanoylloline, N-nonanoylloline, N-decanoylloline, N-dodecanoylloline, N-tetradecanoylloline, and N-(p-hexylbenxoyl)loline were generally 2-fold lower for annual ryegrass than for alfalfa. N-(cyclopropanecarboxyl)loline was slightly selective against alfalfa seedling length. Compounds that were phytotoxic, but nonselective, include N-(3-methyl-2-butenoyl)loline (seedling growth inhibition) and N-cinnamoylloline (both seed germination and seedling growth inhibition).

The results are shown in Table I.

Phytotoxic activity against seedling length of a representative straight-chain N-acylloline derivative, N-dodecanoylloline, was compared with the activity of two known allelochemicals and a commercial grass herbicide. The phytotoxicity of N-dodecanoylloline was comparable to that of juglone and plumbagin (Dornbos et al., J. Chem. Ecol. 16(2): 339–352 (1990).

TABLE I

Inhibition of Alfalfa and Annual Ryegrass Seed
Germination and Seedling Growth by Loline and Selected Derivatives[a]

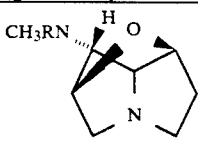

| Compound | R | Germination %, $ID_{50}$ | | Seedling Length, $ID_{50}$ | |
|---|---|---|---|---|---|
| | | alfalfa | annual ryegrass | alfalfa | annual ryegrass |
| 1 | H | > | > | > | > |
| 2 | formyl | > | 77 | > | > |
| 3 | acetyl | > | > | > | > |
| 4 | propionyl | > | > | > | > |
| 5 | butyryl | > | 90 | > | 54 |
| 6 | n-hexanoyl | > | 147 | 66 | 15 |
| 7 | n-octanoyl | 101 | 42 | 19 | 19 |
| 8 | n-nonanoyl | 47 | 34 | 12 | 6 |
| 9 | n-decanoyl | 43 | 11 | 16 | 7 |
| 10 | n-dodecanoyl | > | 6 | 7 | 5 |
| 11 | n-tetradecanoyl | 51 | 47 | 8 | 6 |
| 12 | n-hexadecanoyl | > | > | 27 | 30 |
| 13 | methyl | > | 124 | > | > |
| 14 | isobutyryl | > | 144 | > | > |
| 15 | cyclopropanecarboxyl | > | > | 91 | > |
| 16 | benzoyl | > | > | 50 | 71 |
| 17 | cinnamoyl | 48 | 97 | 35 | 49 |
| 18 | p-n-hexylbenzoyl | 86 | 6 | 8 | 5 |
| 19 | 3-methyl-2-butenoyl | > | > | 107 | > |

[a]Values are expressed as the dose ($\times 10^{-8}$ mol/seed) that gives 50% inhibition of seed germination or seedling length ($ID_{50}$).
> indicates that a toxic dose may exist at doses greater than those used in our bioassay. At such higher doses, the compound would not be considered useful as a potential herbicide. The length of each seedling (root plus shoot) was measured to the nearest millimeter.

Two Choice Diet Incorporated Insect Feeding Behavior Modification Bioassay

Loline and loline derivatives were dissolved in solvent (methanol or methylene chloride depending upon solubility) and applied to powdered cellulose. After drying, the cellulose powder-loline derivative mixtures were placed into test tubes (7.5 × 1.0 cm), and the tube was filled to the 4-cm mark with liquid artificial fall armyworm diet medium (Bioserv #F9179). Test tube contents were thoroughly mixed and the diet medium was drawn into a plastic soda straw (0.5 cm diameter) to a height of 10 cm. After solidification, the diet medium was pushed out of the straw and cut into 0.5 cm sections. Final loline derivative concentration in the diet was 2000 ppm. Two sections containing the compound to be tested were placed opposite one another, in a 5-cm petri dish. In the same dish, also placed opposite one another, were two sections of diet that were prepared the same way, using the same solvent but containing no loline derivatives. Each diet section was equidistant from the one next to it and approximately 0.5 cm from the edge of the petri dish.

Twenty newly hatched fall armyworm or European corn borer larvae were placed into each petri dish. Each petri dish containing insects was placed in darkness at 27° C. for 16 to 20 hr; following this the dishes and contents were frozen. The number of larvae present on each diet type, as well as nonresponding larvae in each dish, were recorded. The feeding behavior modification bioassay was a test patterned after that used to study phagostimulants for European corn borers of Bartelt et al. [Environ. Entomol. 19: 182-189 (1990)]. Newly hatched larvae typically wander about the petri dish for several hours, appearing to "taste" the diet materials they encounter. Within 16-20 hr, they settle down to feed on an acceptable piece of diet and remain there; the corn borer larvae also produce a silk "nest" at their feeding site. In preliminary observations, the larvae did not leave these feeding sites when the petri dish was placed in the freezer. Freezing facilitated counting all of the larvae at each diet section but did not change the larvae distribution. The number of nonresponding larvae in the tests was generally less than 10%, because at least the control diet was readily accepted by the larvae of both species. The final distribution of larvae was interpreted as a measure of feeding behavior modification. If the larvae were equally distributed between the two types of diet, then there was no evidence for feeding modification; but if the larvae were found at the control diet, then the test was concluded to modify feed behavior. Statistical analysis was by Chi-square tests. The null hypothesis was a 50:50 distribution of larvae between the test and control diets. A significant Chi-square statistic (P is less than 0.05) was evidence for a difference from the control. Using five replicates gave greater power to this Chi-square test and also allowed the consistency ratio, treatment:control, to be evaluated among replications, again with Chi-square tests. These tests were non-significant (P is greater than 0.05) in almost all cases, indicating the data were "well-behaved" and that the Chi-square test for detecting differences between treatments and controls was appropriate. The data were summarized as "larvae distribution ratios," defined as the total number of larvae at the treatment divided by total at the control diet.

No Choice Toxicity Bioassay

Toxicity tests involved incorporating samples into diet in the same manner as shown above. Fifty milligrams of sample was incorporated into 2.5 g of liquid diet and then drawn into 5 soda straws to the 21 cm mark in each. After solidification, the straws were cut into 3-cm sections and placed one per cup (cups were clear plastic with a 1-oz volume). Newly hatched fall armyworm or European corn borer larvae (15 per trial, 1 larvae per cup) were placed in cups containing treated diets as well as controls containing diet only and diet plus solvent (replicated 5 times). Insects were allowed to feed for 8-9 days, at which time mortality and weights of surviving insects were recorded. Significant differences within larvae weight ratios were determined by ANOVA.

Greenbug Toxicity Studies

Clones of field-collected greenbug were maintained in culture on seedlings of barley in a growth chamber under 16 hr photoperiods at 23° C. and 85% relative humidity.

Ten adult apterous greenbugs were transferred to 8-day-old barley plants (one leaf fully expanded) which was then covered with a 7×40 cm vented, clear plastic tubular cage. After the greenbugs were on the plants 24 hr, the plants were sprayed with loline derivative solutions. Immature greenbugs born during the 24 hr were not removed before spraying. Loline derivatives were dissolved in 95% ethanol, which was quantitatively added to application solutions which contained a final concentration of 0.05% (v:v) polyoxyethylene sorbitan monooleate (a surfactant). Solutions containing 0, 400, or 4000 μg/ml nicotine sulfate, loline, or loline derivatives were applied to plants using a thin-layer chromatographic atomizer, and the cages were replaced. Each cage was inspected for wandering greenbug adults 2 hr after spray application. The number of live apterous adult greenbugs, as well as the number of dead adult greenbugs, was determined 18 hr after spray application. Each concentration of each loline derivative tested was replicated 3 times. Greenbug-infested plants sprayed with solutions containing the same concentrations of ethanol and polyoxyethylene sorbitan monooleate served as controls.

The amount of solution sprayed on each plant was previously measured on uninfected plants. Plants were clipped below soil level and weighed. The clipped plants were placed back in the pot, held in an upright position with soil. After spraying with the atomizer, plants were immediately weighed again. The difference in weight before and after spraying was approximately 46 mg.

From the data presented in Table II, it is clear that some tested compounds had significant effects upon the feeding behavior of fall armyworm larvae and European corn borer larvae. The number of fall armyworm larvae feeding on diet treated with 2000 ppm loline derivatives divided by the number of larvae feeding on untreated diet (larvae distribution ratios) was significantly reduced by a greater number of compounds tested and to a greater extent than the larvae distribution ratios of the European corn borer larvae. This species response differential was also evident in weights of larvae. Fall armyworm larvae tended to show slower weight gain than European corn borer larvae. Compounds that caused significant effects on both species in both parameters studied include N-lauroylloline, N-palmitoylloline, and N-cinnamoylloline.

In the two-choice antifeeding bioassay, the number of non-responding insects was low. The number of non-responding European corn borer larvae averaged less than 10% per treatment with a range of 0-19% (data not shown). For fall armyworm larvae, nonresponse averaged 11% per sample with a range of 0-47% nonresponse. The compounds N-propinoyl- and N-butyrylloline showed unusually high non-response (47% and 43%, respectively). Because the responding larvae showed no preference between treated and control diets, this phenomenon was not further investigated.

In the no-choice toxicity test, European corn borer larvae had no mortality in either samples or controls after 9 days. Larvae in the 7 control groups had a mean weight gain of 19.5 mg (range of 13.5 to 24.8 mg). In the fall armyworm, larvae in the 7 control groups had a mean weight gain of 84.6 mg (range of 70.3 to 103.8 mg). Mean mortality in the control groups was 10% after 8 days (range of 0-20%). N-formylloline has the highest mortality of the samples tested (33%). Chi-square analysis indicated this was very close to being active at the 99% level. No other sample had greater than 15% mortality.

TABLE II

| | Results of Loline Bioassays Against Fall Armyworms and European Corn Borers (2000 ppm) | | | |
|---|---|---|---|---|
| | ARMYWORMS | | CORNBORERS | |
| Compound Name | 2-Choice Test Larvae Distribution Ratio | No-Choice Test Larval Weight Ratio$^\pm$ | 2-Choice Test Larvae Distribution Ratio | No-Choice Test Larval Weight Ratio$^\pm$ |
| Loline | 0.70 | 92 | 0.60 | 150 |
| N-formylloline | 0.24***= | 40*** | 0.73 | 89 |
| N-acetylloline | 0.71 | 71** | 0.86 | 60** |
| N-methylloline | 0.65 | 95 | 0.65 | 147 |
| N-propionylloline | 0.96 | 89 | 0.94 | 61 |
| N-butyrylloline | 0.84 | 70** | 0.59* | 76 |
| N-isobutyrylloline | 0.39*** | 100 | 0.85 | 75 |
| N-cyclopropane-carboxylloline | 0.56** | 89 | 1.12 | 76 |
| N-hexanoylloline | 0.42*** | 98 | 0.92 | 104 |
| N-octanoylloline | 0.27*** | 77* | 1.00 | 71* |
| N-nonanoylloline | 0.12*** | 58*** | 1.11 | 48** |
| N-decanoylloline | 0.11*** | 49*** | 1.25 | 46*** |
| N-lauroylloline | 0.12*** | 38*** | 0.61* | 67* |
| N-myristoylloline | 0.11*** | 48*** | 0.81 | 81 |
| N-palmitoylloline | 0.07*** | 6*** | 0.58* | 42*** |

TABLE II-continued

Results of Loline Bioassays Against Fall Armyworms and European Corn Borers (2000 ppm)

| | ARMYWORMS | | CORNBORERS | |
|---|---|---|---|---|
| Compound Name | 2-Choice Test Larvae Distribution Ratio | No-Choice Test Larval Weight Ratio± | 2-Choice Test Larvae Distribution Ratio | No-Choice Test Larval Weight Ratio± |
| N-benzoylloline | 0.36*** | 48*** | 0.56* | 85 |
| N-cinnamoylloline | 0.29*** | 62*** | 0.45*** | 58** |
| N-hexylbenzoyl-loline | 0.10*** | 57*** | 0.94 | 42*** |
| N-dimethylacroyl-loline | 0.62* | 78* | 0.71 | 83 |

Feeding ratio = # of larvae on treated diet/# of larvae on control diet.
±Larval weight = mean larval weight for treated diet/mean larval weight for control diet ($\times$ 100).
= *, , * - represent significant differences from the controls at the 95%, 99%, 99.9% confidence levels using chi-square analysis for two-choice tests and ANOVA for larval weight data.

Results of screening various concentrations of loline derivatives for toxicity against greenbugs are shown in Table III. Nicotine sulfate, a contact insecticide, was also included in this test. Two hours after spray application, no difference in greenbug behavior (wandering) was apparent (data not shown). Results of greenbug counts taken 18 hr after spraying indicated that several compounds showed toxicity equal to or greater than nicotine sulfate against adult greenbugs at concentrations of 4000 μg/ml of spray solution. These compounds include N-formylloline, N-acetylloline, N-methylloline, N-propionylloline, and N-myristoylloline. These compounds were further tested to determine $LC_{50}$. Activities of several loline derivatives compare favorably with nicotine sulfate, Table IV. The slopes of the regression lines for all of the loline derivatives tested, with the exception of N-methylloline, were similar. The slopes of the regression lines for nicotine sulfate and N-methylloline were also similar.

Various modifications and alterations of this invention will become apparent to those skilled in the art without departing from the scope and spirit of this invention, and it should be understood that this invention is not limited to the illustrative embodiments set forth herein.

TABLE III

Average Number of Greenbugs Alive on Plants After Spray Treatment with Nicotine Sulfate, Loline, or Loline Derivatives Tested at 0, 400, and 4000 μg/ml

| Compound Name | # of Alive Greenbugs* 0 | # of Alive Greenbugs* 400 μg/ml | # of Alive Greenbugs* 4000 μg/ml |
|---|---|---|---|
| Nicotine sulfate | 8.3 ± 0.9 | 3.3 ± 0.7 | 0.3 ± 0.3 |
| Loline | 6.6 ± 1.2 | 7.7 ± 1.2 | 3.3 ± 0.8 |
| N-formylloline | 6.7 ± 1.8 | 7.7 ± 0.9 | 0 |
| N-acetylloline | 8.3 ± 1.2 | 2.5 ± 0.5 | 0 |
| N-methylloline | 7.7 ± 1.3 | 3.7 ± 0.9 | 0.3 ± 0.3 |
| N-propionylloline | 6.7 ± 0.3 | 5.0 | 0.3 ± 0.3 |
| N-butyrylloline | 7.0 ± 0.6 | 8.0 ± 0.6 | 3.0 ± 0.6 |
| N-isobutyrylloline | 7.3 ± 1.2 | 7.0 ± 1.2 | 4.7 ± 1.3 |
| N-cyclopropanecarboxyl-loline | 7.0 ± 1.5 | 6.0 ± 0.6 | 2.3 ± 0.3 |
| N-hexanoylloline | 7.7 ± 0.9 | 6.7 ± 1.9 | 7.0 ± 0.6 |
| N-octanoylloline | 7.7 ± 1.2 | 5.0 ± 1.5 | 6.0 ± 0.6 |
| N-nonanoylloline | 5.0 ± 2.1 | 6.0 ± 0.6 | 6.3 ± 1.8 |
| N-decanoylloline | 6.0 ± 1.5 | 7.3 ± 0.9 | 1.7 ± 1.2 |
| N-lauroylloline | 7.7 ± 0.3 | 5.7 ± 0.9 | 2.3 ± 1.5 |
| N-myristoylloline | 8.7 ± 1.2 | 6.3 ± 0.7 | 0.3 ± 0.3 |
| N-palmitoylloline | 6.0 ± 1.0 | 5.7 ± 0.7 | 3.0 ± 0.6 |
| N-benzoylloline | 8.0 ± 1.0 | 6.7 ± 1.3 | 5.7 ± 0.9 |
| N-hexylbenzoylloline | 6.7 ± 1.8 | 7.0 ± 1.5 | 5.7 ± 0.3 |
| N-dimethylacroylloline | 5.3 ± 0.9 | 8.0 ± 0.6 | 1.3 ± 0.7 |
| N-nicotanoylloline | 7.0 ± 1.5 | 9.3 ± 0.7 | 6.3 ± 1.8 |

*Values represent mean ± SE

TABLE IV

Average $LC_{50}$ Values and Confidence Intervals for Nicotine Sulfate and Selected Loline Derivatives for Adult Greenbugs

| Compound Name | Concentration Range Tested μg/ml* | LC50 | .95 C.I. | Slope + |
|---|---|---|---|---|
| Nicotine sulfate | 0–4,000 | 199 | 45–459 | 1.2 ± 0.3 |
| N-formylloline | 0–3,300 | 437 | 237–615 | 3.1 ± 0.7 |
| N-acetylloline | 0–500 | 343 | 190–532 | 2.3 ± 0.8 |
| N-methylloline | 0–4,000 | 361 | 81–613 | 1.6 ± 0.4 |
| N-propionylloline | 0–4,000 | 551 | 234–907 | 2.5 ± 0.5 |
| N-myristoylloline | 0–4,000 | 1,683 | 1,115–3,109 | 3.9 ± 0.9 |

*Between 6 and 14 different concentrations within the ranges indicated, replicated 3 times, were evaluated for each compound.
+ Values represent slope ± SE

We claim:
1. Compounds of the formula

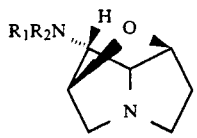

wherein $R_1$ is a $C_6$ to $C_{20}$ aliphatic, aromatic, or alicyclic hydrocarbon optionally substituted with oxygen, and $R_2$ is H, or an aliphatic, aromatic, or alicyclic hydrocarbon optionally substituted with oxygen.

2. The compound of claim 1 which is substantially pure.

3. The compound of claim 1 wherein $R_2$ is $CH_3$.

4. The compound of claim 3 wherein $R_1$ is an acyl group.

5. The compound of claim 4 wherein the acyl group is $C_9$ to $C_{14}$.

6. The compound of claim 4 wherein the acyl group is selected from the group consisting of n-hexanoyl, n-octanoyl, n-nonanoyl, n-decanoyl, n-dodecanoyl, n-tetradecanoyl, n-hexadecanoyl, benzoyl, cinnamoyl, and p-n-hexylbenzoyl.

7. The compound of claim 1, wherein $R_2$ is H.

8. The compound of claim 7 wherein $R_1$ is an acyl group.

9. The compound of claim 8 wherein the acyl group is $C_9$ to $C_{14}$.

10. A composition of the compound of claim 1 and a carrier.

11. The composition of claim 10 wherein the compound is substantially pure.

12. The composition of claim 10 wherein $R_2$ is $CH_3$.

13. The composition of claim 12 wherein $R_1$ is an acyl group.

14. The composition of claim 13 wherein the acyl group is $C_9$ to $C_{14}$.

15. The composition of claim 13 wherein the acyl group is selected from the group consisting of n-hexanoyl, n-octanoyl, n-nonanoyl, n-decanoyl, n-dodecanoyl, n-tetradecanoyl, n-hexadecanoyl, benzoyl, cinnamoyl, and p-n-hexylbenzoyl.

16. The composition of claim 10 wherein $R_2$ is H.

17. The composition of claim 16 wherein $R_1$ is an acyl group.

18. The composition of claim 17 wherein the acyl group is $C_9$ to $C_{14}$.

19. A method for controlling plant growth comprising the step of providing to the locus of a plant or seed a herbicidally effective amount of the compound of claim 1.

20. The method of controlling insects comprising applying to the locus of said insects an insecticidally effective amount of the compound of claim 1.

21. Compounds of the formula

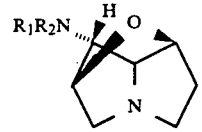

wherein $R_1$ is a $C_4$ or $C_5$ aliphatic, aromatic, or alicyclic hydrocarbon optionally substituted with oxygen, and $R_2$ is an aliphatic, aromatic, or alicyclic hydrocarbon optionally substituted with oxygen.

22. The compound of claim 21 being substantially pure.

23. The compound of claim 21 wherein $R_1$ is an acyl group.

24. The compound of claim 23 wherein $R_1$ is selected from the group consisting of butyryl, isobutyryl, cyclopropanecarboxyl, and 3-methyl-2-butenoyl.

25. A composition comprising the compound of claim 21 and a carrier.

26. The composition of claim 25 wherein the compound is substantially pure.

27. The composition of claim 25 wherein $R_1$ is an acyl group.

28. The composition of claim 27 wherein $R_1$ is selected from the group consisting of butyryl, isobutyryl, cyclopropancarboxyl, and 3-methyl-2-butenoyl.

29. A method for controlling plant growth comprising the step of providing to the locus of a plant or seed a herbicidally effective amount of the compound of claim 21.

30. A method of controlling insects comprising the step of applying to the locus of said insects an insecticidally effective amount of the compound of claim 21.

31. The compound of claim 23 wherein $R_2$ is $CH_3$.

32. The composition of claim 27 wherein $R_2$ is $CH_3$.

* * * * *